(12) United States Patent
Roh et al.

(10) Patent No.: US 11,304,760 B1
(45) Date of Patent: Apr. 19, 2022

(54) CUSTOMIZED KIT ASSEMBLY FOR SURGICAL IMPLANTS

(71) Applicant: IX Innovation LLC, Seattle, WA (US)

(72) Inventors: Jeffrey Roh, Seattle, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/495,395

(22) Filed: Oct. 6, 2021

(51) Int. Cl.
| | | |
|---|---|---|
| *A61B 34/10* | (2016.01) | |
| *A61B 34/30* | (2016.01) | |
| *A61F 2/30* | (2006.01) | |

(52) U.S. Cl.
CPC .............. *A61B 34/10* (2016.02); *A61B 34/30* (2016.02); *A61F 2/30942* (2013.01); *A61B 2034/108* (2016.02); *A61F 2002/3097* (2013.01); *A61F 2002/30948* (2013.01); *A61F 2002/30952* (2013.01); *A61F 2002/30968* (2013.01); *A61F 2002/30985* (2013.01)

(58) Field of Classification Search
CPC ......... A61B 34/10; A61B 34/20; A61B 34/25; A61B 34/00; A61B 17/70; A61B 90/37; G06T 7/73; G06T 19/00
See application file for complete search history.

(56) References Cited

U.S. PATENT DOCUMENTS

| | | | | |
|---|---|---|---|---|
| 9,849,019 B2* | 12/2017 | Miller | ................. | A61F 2/30942 |
| 11,112,770 B2* | 9/2021 | Roh | ...................... | G16H 30/40 |
| 11,166,764 B2* | 11/2021 | Roh | ...................... | G16H 20/40 |

* cited by examiner

*Primary Examiner* — Christopher J Beccia
(74) *Attorney, Agent, or Firm* — Perkins Coie LLP

(57) ABSTRACT

Methods, apparatuses, and systems for customized kit assembly for surgical implants are disclosed. A robotic surgical system designs and customizes a surgical implant and its surgical implant components. The surgical implant and its surgical implant components are assembled into a kit that is customized for a specific patient. The robotic surgical procedure using the kit can additionally select from available generic, off-the-shelf surgical implant components or customized surgical implant components.

20 Claims, 11 Drawing Sheets

| Implant ID | Implant Type | Patient ID | Age | Gender | Height (in.) | Implant Component ID | Component Type | Length (in.) | Diameter/ Thickness (in.) | Material | Generic/ Custom |
|---|---|---|---|---|---|---|---|---|---|---|---|
| SF-00345 | Spinal Fusion | 32163 | 57 | Female | 66 | SF-00345-003 | Screw | 1.5 | 0.25 | Titanium | Generic |
| SF-00345 | Spinal Fusion | 32163 | 57 | Female | 66 | SF-00345-004 | Screw | 2 | 0.25 | Titanium | Generic |
| SF-00345 | Spinal Fusion | 32163 | 57 | Female | 66 | SF-00345-005 | Screw | 1.5 | 0.1875 | Titanium | Custom |
| SF-00345 | Spinal Fusion | 32163 | 57 | Female | 66 | SF-00345-006 | Rod | 3.5 | 0.375 | Titanium | Custom |
| SF-00345 | Spinal Fusion | 32163 | 57 | Female | 66 | SF-00345-007 | Rod | 4 | 0.5 | Titanium | Generic |
| SF-00345 | Spinal Fusion | 32163 | 57 | Female | 66 | SF-00345-008 | Plate | 2.5 | 0.375 | Titanium | Custom |
| SF-02345 | Spinal Fusion | 35468 | 64 | Male | 75 | SF-02345-001 | Screw | 2 | 0.25 | Stainless Steel | Generic |
| SF-02345 | Spinal Fusion | 35468 | 64 | Male | 75 | SF-02345-002 | Screw | 1.75 | 0.1875 | Stainless Steel | Custom |
| SF-02345 | Spinal Fusion | 35468 | 64 | Male | 75 | SF-02345-003 | Screw | 1.5 | 0.1875 | Stainless Steel | Custom |

*FIG. 7*

CUSTOMIZED KIT ASSEMBLY FOR SURGICAL IMPLANTS

TECHNICAL FIELD

The present disclosure is generally related to automated and robotic surgical procedures and specifically to systems and methods for providing kit assemblies for surgical implants.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 is a table illustrating an example surgical implant database, in accordance with one or more embodiments.

DETAILED DESCRIPTION

Figure 1:
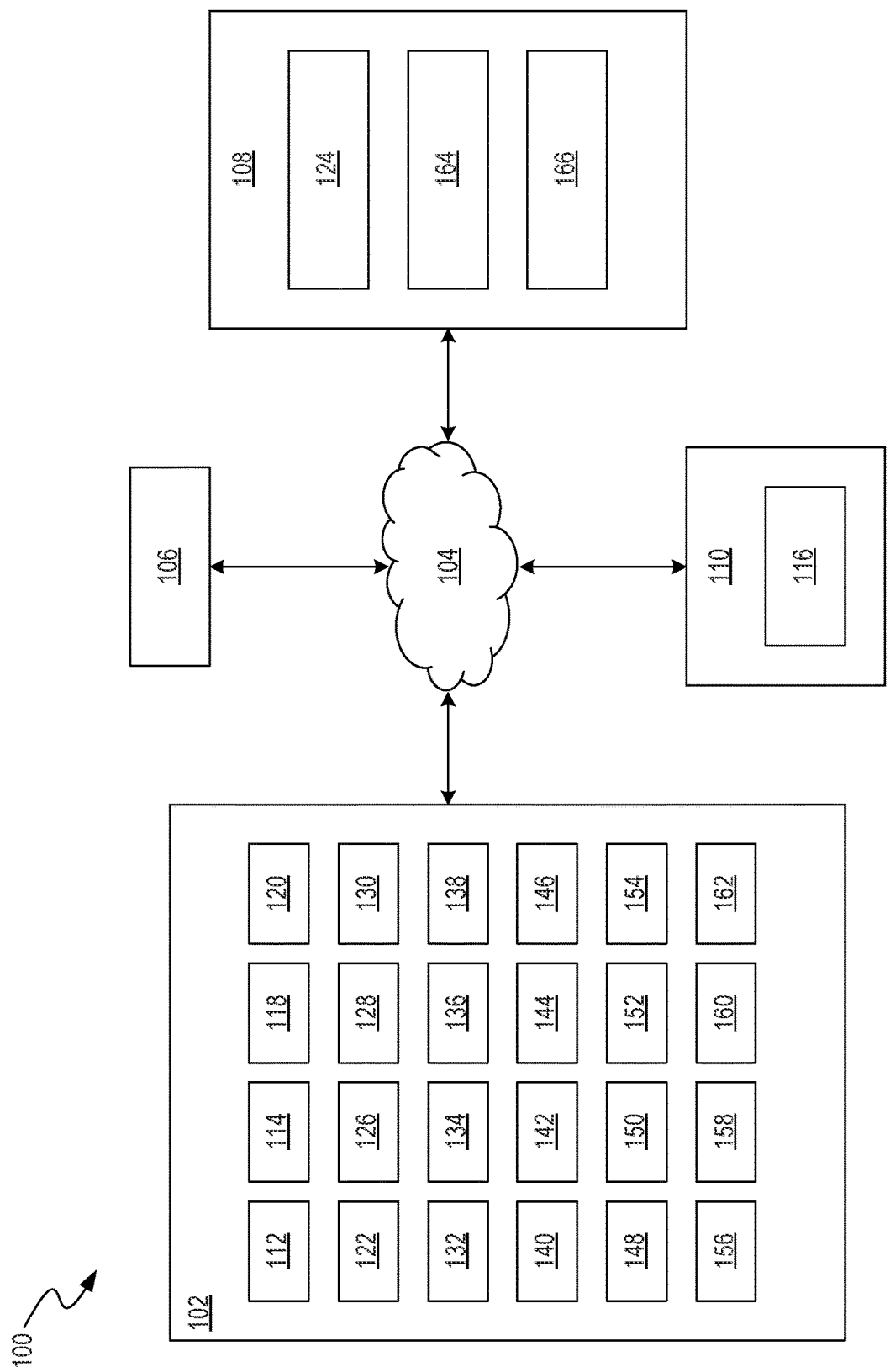
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "602") may implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

A surgical implant refers to a medical device manufactured to replace a missing biological structure, support a damaged biological structure, or enhance an existing biological structure. A surgical implant can include generic, off-the-shelf parts as well as customized parts. While each of off-the-shelf parts and customized parts have their advantages, each can have drawbacks. Generic components are typically cheaper, however, they can be less than ideal for a particular patient and can result in uncomfortable stiffness or restricted movement. Generic parts are readily available for emergency procedures but can require a follow up surgery to correct problems arising from surgical implants that are not customized for a particular patient or application. A follow up surgery can add cost or negatively impact a patient's wellbeing. Surgical implants that are customized to a patient or a specific application can offset the drawbacks of surgical implants made from generic parts, however, customized surgical implants can be more expensive. Customized surgical implants may also not be readily available, requiring time to design, construct, and then deliver the surgical implant components to be implanted in a patient. Therefore, fully customized surgical implants can sometimes be impractical for emergency surgery.

Customized surgical implants can include generic parts, such as fixation screws, in addition to customized surgical implant components. The different types of surgical implant components may need to be sourced independently, with the generic surgical implant components being sourced from one distributer while the customized parts are manufactured by a different distributor or possibly even on site where the implantation procedure takes place. Sometimes, generic surgical implant components can be customized through modifications that are performed by a surgeon during the implantation procedure.

The embodiments disclosed herein describe methods, apparatuses, and systems for customized kit assembly for surgical implants. In some embodiments, a robotic surgical system designs and customizes a surgical implant and its surgical implant components. The surgical implant and its surgical implant components are assembled into a kit that is customized for a specific patient. The robotic surgical procedure using the kit can additionally select from available generic, off-the-shelf surgical implant components or customized surgical implant components.

In some embodiments, a surgical kit can be made available for a surgical procedure by selecting a generic surgical implant and then producing, for example, by 3D printing, a customized implant. A surgical implant can be rigid, such as when reinforcing bone structures, or can be flexible, such as when replacing or supplementing soft tissues. Similarly, a surgical implant can be static and unmoving, or can include articulating joints or other moveable elements. A surgical implant can include any of a range of materials, each of which can have different properties such as being rigid or flexible. Multiple materials can be utilized in the different surgical implant components or where the surgical implant components meet to perform different functions, creating more complex implants. The implant components can be generic, off-the-shelf implant components or components that are or can be modified or customized for a particular patient using the embodiment described herein. A surgical implant can be a single piece or can include multiple surgical implant components. Surgical implants that include multiple implant components can alternatively be referred to as assemblies. An implant can be customized to fit a particular patient or a specific application that the implant is intended for. For example, an implant can include biological donor tissues or biosynthetic tissues such as can be used in operations such as organ transplant, skin graft, or other tissue installation or replacement. In other examples, an implant can be any of multiple implantable medical devices, e.g., cardiac pacemakers, electric neurological stimulation devices such as vagus nerve stimulators or deep brain stimulators, blood glucose monitors, insulin pumps, etc.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed provides a simplified means of assembling a kit of surgical implant components, such that a surgical implant is customized for a patient or an application while reducing cost. Using the embodiments disclosed, a kit of surgical implant components is provided to reduce cost while customizing a surgical implant for a patient or application. Therefore, the embodiments disclosed herein make customized surgical implants more accessible. In addition, the embodiments consider an amount of time required to source surgical implant components. Hence, longer-term beneficial patient outcomes can be achieved by balancing the customization of surgical implant components, when possible, with the availability of parts and the urgency of a patient's need. For example, surgical implant components can be selected for a patient requiring emergency surgery based not only on what generic parts are on hand, but in addition by customization that can be performed on site, including both the modification of generic parts and the rapid manufacturing of customized parts.

The robotic surgery technologies disclosed further offer valuable enhancements to medical or surgical processes through improved precision, stability, and dexterity. The disclosed methods relieve medical personnel from routine tasks and make medical procedures safer and less costly for patients. The embodiments disclosed enable performing more accurate surgery in more minute locations on or within the human body. The embodiments also address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer. This both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of a target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end-effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool—tissue interaction forces. During MIS, the field of view and workspace of surgical tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for the fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a postoperative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table which is designed for use in spinal surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment 102. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
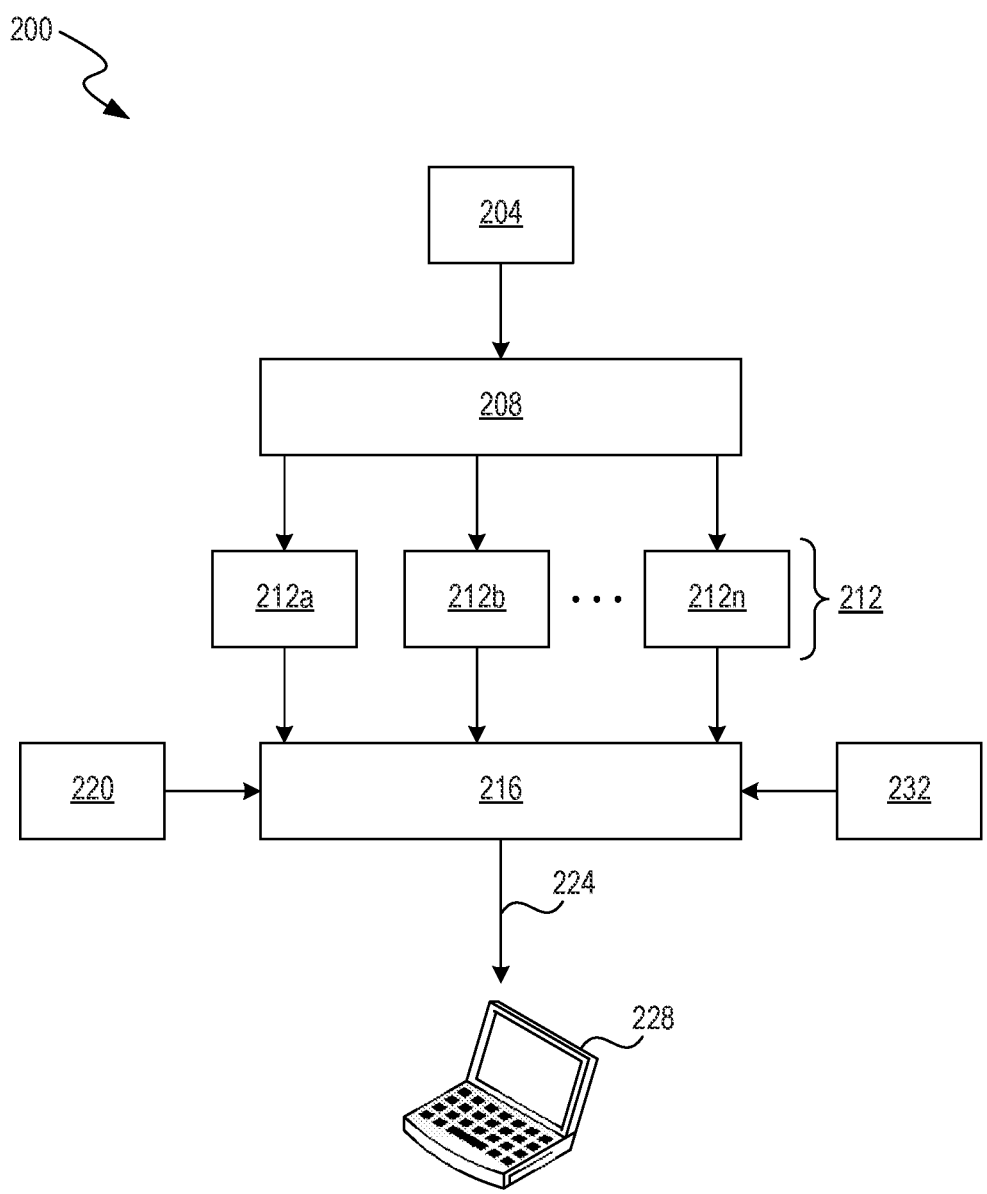
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
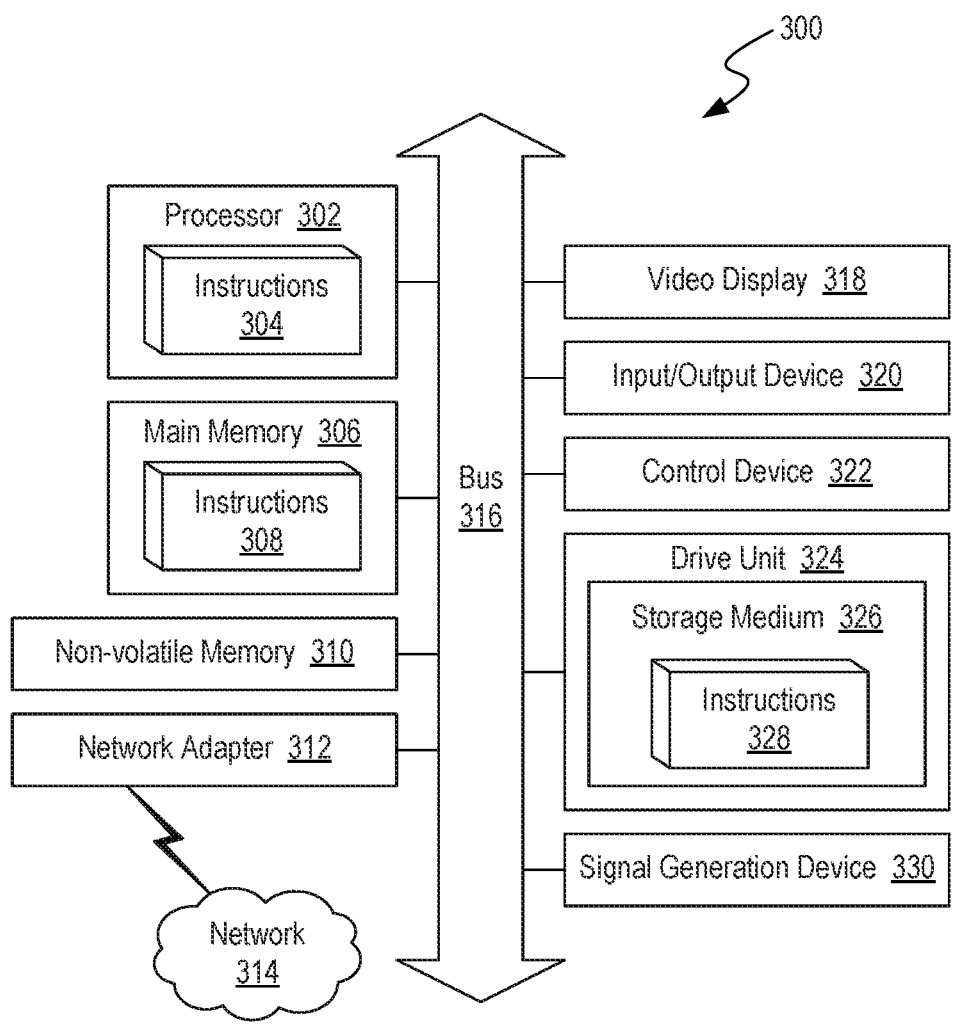
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
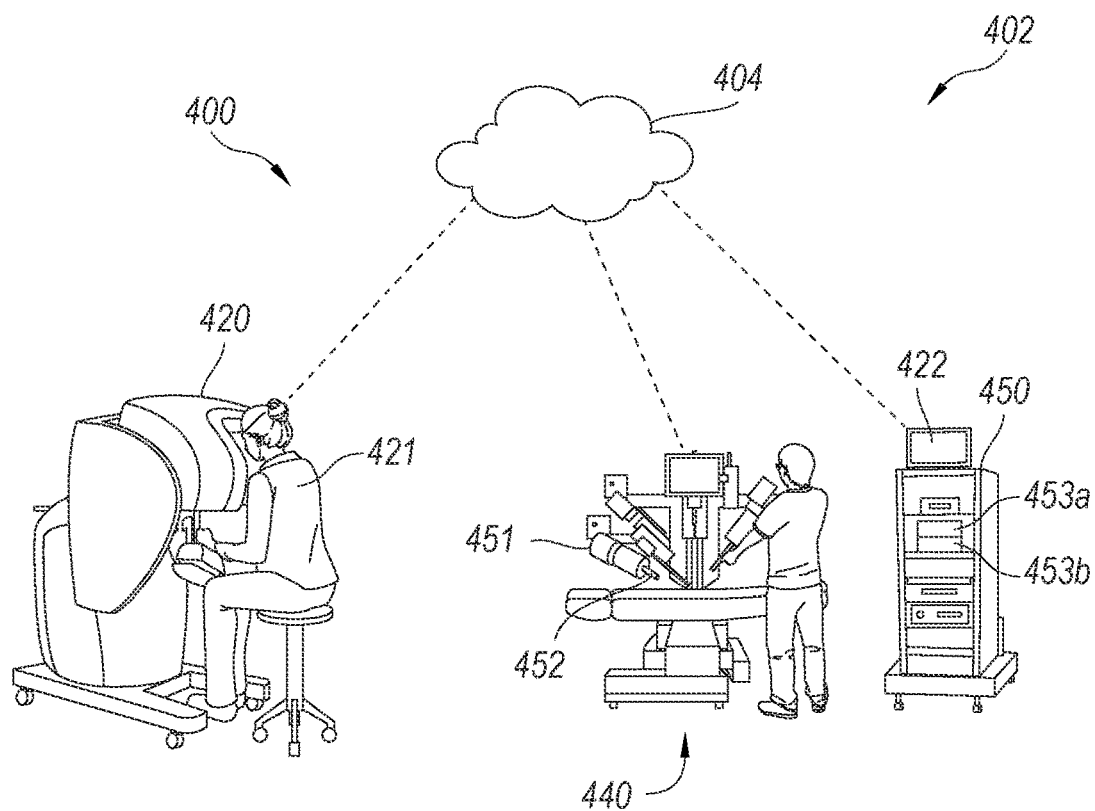
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one or more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include preoperative images, such as MRI, CT, PET, etc. The various imaging modalities can be selectable, programmed, superimposed and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
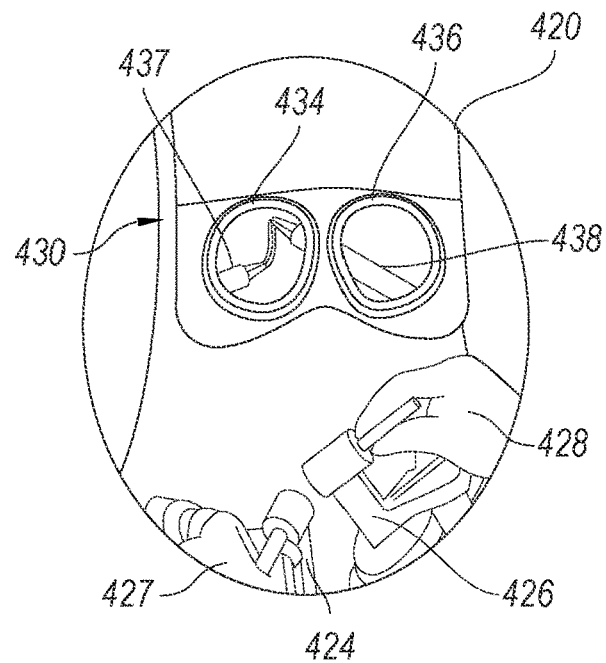
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring.

In some embodiments, the robotic surgical system 400 can determine whether a detected event is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital or on-site inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre- or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively. Kits (e.g., pre-operative kits, intraoperative kits, etc.) can be modified or provided based on the modification.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates an optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and post treatment mapping can be compared by the surgeon and/or ML/AI system. The comparison can be used to determine next steps in a procedure and/or further train the ML/AI system.

Figure 5:
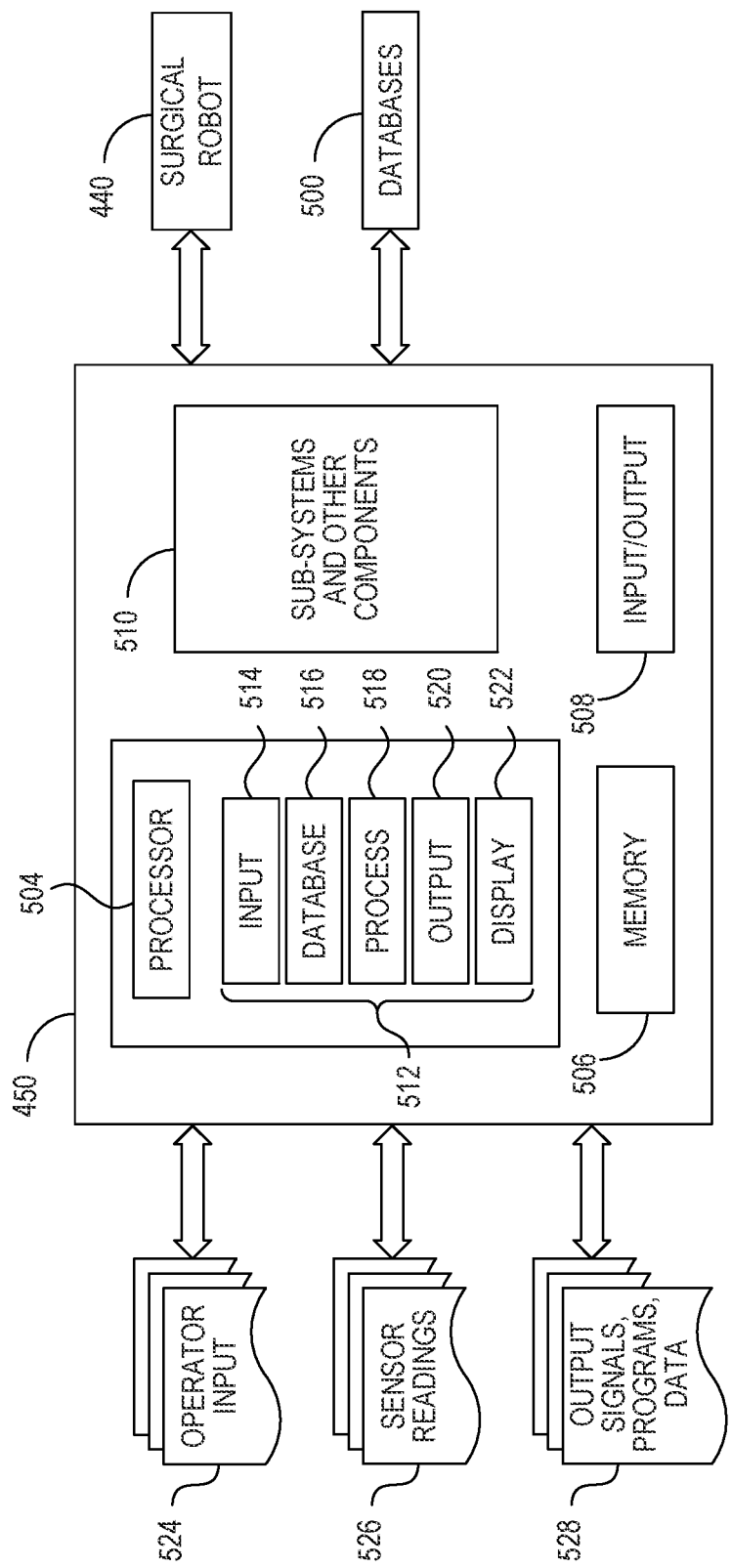
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to improve patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
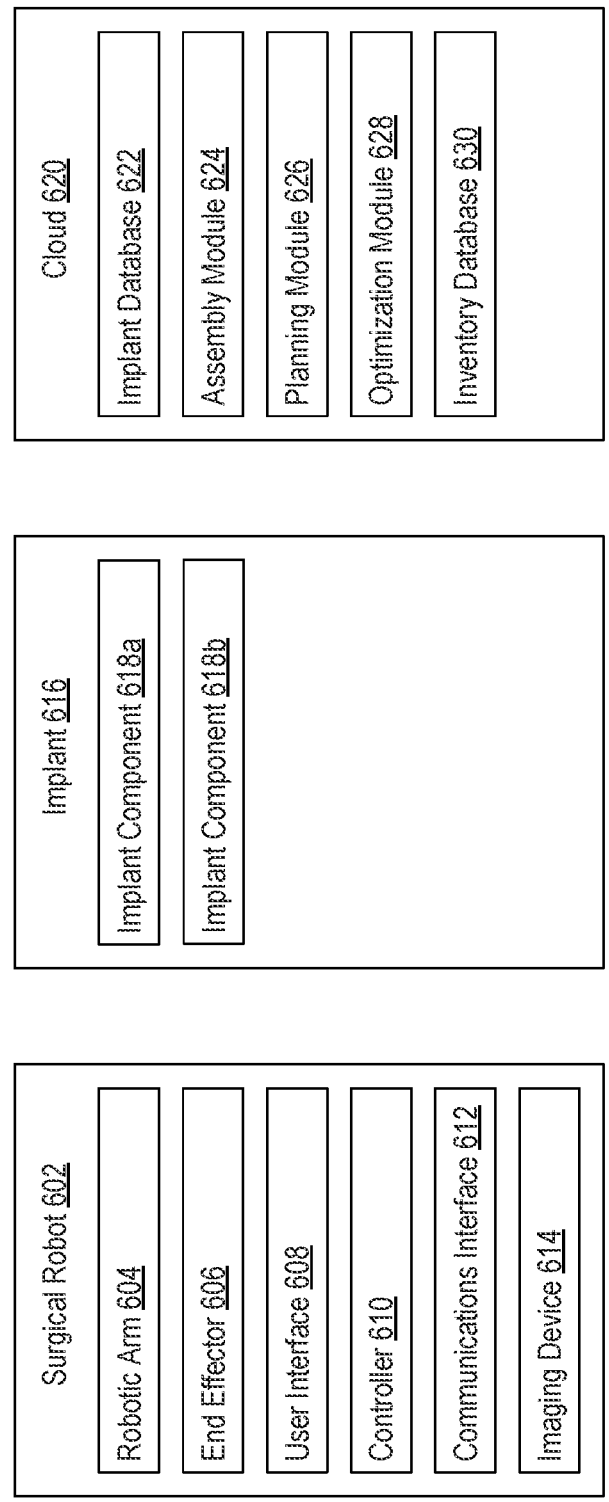
FIG. 6 is a block diagram illustrating an example robotic surgical system for customized kit assembly for surgical implants, in accordance with one or more embodiments.

FIG. 6 is a block diagram illustrating an example robotic surgical system for customized kit assembly for surgical implants, in accordance with one or more embodiments. The implantation of surgical implants or surgical implant components is sometimes referred to as "insertion" or "installation." Surgical implants are sometimes referred to as "implants." Surgical implant components are sometimes referred to as "implant components." The system of FIG. 6 includes at least one surgical robot 602a, databases and modules that can be implemented in the cloud 620, and at least one surgical implant 616. The surgical robot 602 is the same as or similar to the surgical robot 440 illustrated and described in more detail with reference to FIG. 4A. The system is implemented using the components of the example computer system 300 illustrated and described in more detail with reference to FIG. 3. Likewise, embodiments of the system can include different and/or additional components or can be connected in different ways.

The robotic surgical system of FIG. 6 includes a surgical robot 602, which is a robotic system designed to assist a surgeon in performing a surgical operation on a patient. The surgical robot 602 includes at least one controller 610 and at least one robotic arm 604 having an end effector 606 or an imaging device 614. The controller 610 is implemented using the components of the example computer system 300 illustrated and described in more detail with reference to FIG. 3. The surgical robot 602 further includes a user interface 608 for accepting control inputs from a user, such as a surgeon or other medical professional, and a communications interface 612 for transmitting and receiving data to and from a cloud 620 for the purpose of training an artificial intelligence (AI) operating within the surgical robot 602 or receiving remote commands from a remote user or an AI (see FIG. 2) implemented external to the surgical robot 602. The robotic arm 604 is a mechanically actuated arm or lever with at least two degrees of freedom. The robotic arm 604 typically includes at least one end effector 606 or an imaging device 614 and may include both the end effector 606 and the imaging device 614. The robotic arm 604 can additionally be capable of changing the end effector 606 to facilitate multiple functions and operation of a variety of tools. Example surgical tools 154 are illustrated and described in more detail with reference to FIG. 1.

The robotic arm 604 can be manually controlled or operated in an autonomous or semi-autonomous mode. The surgical robot 602 can have one robotic arm 604 or multiple robotic arms 604, each of which can be operated independently by one or more users or autonomous systems or a combination of users and autonomous systems. The end effector 606 is the end of the robotic arm 604 that is conducting work. The end effector 606 is typically a tool or device for interacting with a physical object and can be a surgical tool 154 intended for acting upon or within a patient or can be a gripping device for securing a separate surgical tool 154 to the robotic arm 604. The end effector 606 can be permanently affixed to the end of the robotic arm 604 or can be detachable allowing for a system of interchangeable end effectors 606, which can alternatively be selected and swapped by the robotic arm 604 or multiple robotic arms.

The user interface 608 is a means of interacting with the surgical robot 602 and can include any of a keyboard, computer mouse, trackball, joystick, wireless or wired gamepad, sliders, scroll wheels, touch screen or microphone for receiving voice commands. The user interface can additionally perform other methods of interaction of a user with the surgical robot 602. The user interface 608 can accept direct inputs, such as from a joystick controlling the movement of the robotic arm 604 or indirect inputs such as commands entered on a keyboard or touch screen such as adjusting the sensitivity of a joystick control or the speed of the robotic arm 104's movement in response to a joystick. The controller 610 is a computing device including a processor for completing computations and a memory component for storing data for use in computations. The memory can store data temporarily such as for intermediate values used by the controller 610 to complete complex computations or can include persistent storage for longer term storage of information. The controller 610 is in communication with the communications interface 612 and can further be allowed to control the at least one robotic arm 604 and end effector 606 of the surgical robot 602.

The communications interface 612 allows the surgical robot 602 to communicate with external devices and can include a wireless antenna and transceiver or a port for receiving a cable to facilitate a wired connection. Examples of a wired connection include ethernet, universal serial bus (USB) or a proprietary connection. A wireless communications interface can include any of WiFi, Bluetooth, near field communications (NFC) or a cellular communications interface such as 3G, 4G, LTE, or 5G. The communications interface 612 can connect a user interface to the surgical robot 602 or can facilitate access to a local network or the cloud 620's network to access a remote server and/or database.

In some embodiments, the one or more imaging devices 614 of the surgical system of FIG. 6 generate images of a portion of a particular patient's anatomy or body for implanting the surgical implant 616 in the particular patient's anatomy or body for a particular treatment or medical application. The imaging device 614 is any device capable of detecting sound or electromagnetic waves and assembling a visual representation of the detected waves. The imaging devices 614 can collect waves from any part of the electromagnetic spectrum or sounds at any range of frequencies, often as a matrix of independently acquired measurements which each represent a pixel of a two or three-dimensional image. These measurements can be taken simultaneously or in series via a scanning process or a combination of methods. Some pixels of an image produced by an imaging device can be interpolated from direct measurements representing adjacent pixels in order to increase the resolution of a generated image.

The imaging devices 614 can receive or generate imaging data from multiple devices. The multiple devices can include, for example, cameras attached to the robotic arm 604, cameras mounted to the ceiling or other above the surgical theater, cameras that can be mounted on a tripod or other independent mounting device, cameras that can be body worn by the surgeon or other surgical staff, cameras that can be incorporated into a wearable device, such as an augmented reality device such as Google Glass™, cameras that can be integrated to an endoscopic, microscopic, laparoscopic, or any camera or other imaging device (e.g., ultrasound) that can be present in the surgical theater. The imaging device 614 can include any algorithm or software module capable of determining qualitative or quantitative data from medical images, which can be, for example, a deep learning algorithm that has been trained on a data set of medical images (see FIG. 2). The implant 616 is a therapeutic prosthetic device intended to reinforce or restore functionality to a part of a body which has been impacted by an injury, typically traumatic, or a degenerative disease which can result in the loss or destruction of a part of the body.

The surgical implants 616 can be rigid, such as when reinforcing bone structures, or can be flexible, such as when replacing or supplementing soft tissues. Similarly, the surgical implant 616 can be static and unmoving, or can include articulating joints or other moveable elements. The surgical implant 616 can include any of a range of materials, each of which can have different properties such as being rigid or flexible. Multiple materials can be utilized in the different surgical implant components 618 or where the surgical implant components 618 meet to perform different functions, creating more complex implants. The implant components 618a are generic, off-the-shelf implant components while the implant components 618b are implant components that can be or have been modified or customized for a particular patient using the embodiment described herein. The surgical implant 616 can be a single piece or can include multiple surgical implant components 618. Surgical implants that include multiple implant components 618 can alternatively be referred to as assemblies. The implants 616 can be customized to fit a particular patient or a specific application that the implant 616 is intended for. For example, the implant 616 can include biological donor tissues or biosynthetic tissues such as can be used in operations such as organ transplant, skin graft, or other tissue installation or replacement. In other examples, the implant 616 can be any of multiple implantable medical devices, e.g., cardiac pacemakers, electric neurological stimulation devices such as vagus nerve stimulators or deep brain stimulators, blood glucose monitors, insulin pumps, etc.

The implant component 618 is a single manufacturable component of an implant. The implant component 618 can include subassemblies such as hinges, balls, and sockets to create joints or simple components such as screws, rods, plates, and other components which can be included in the implant 616. The implant components 618b can be customized when they are manufactured, or alternatively, before or during implantation. The cloud 620 is a distributed network of computers comprising servers and databases. The cloud 620 can be a private cloud, where access is restricted by isolating the network such as preventing external access, or by using encryption to limit access to only authorized users. Alternatively, the cloud 620 can be a public cloud where access is widely available via the internet. A public cloud may not be secured or can be include limited security features. A historical treatment database or implant database 622 stores data from previously installed implants. The data describes the design and implantation of the previous implants, the tool paths used during the previous implantation procedures, and previous patient information such as gender, age, height, weight, medical conditions, allergies, or vital information such as baseline measurements of heart rate, blood pressure, blood oxygen saturation, or respiration rate.

The implant database 622 is sometimes referred to as a historical treatment database. The implant database 622 is populated with data from the assembly module 624, medical professionals such as surgeons, physicians, nurses, or physical therapists, or from surveys of previous patient outcomes to evaluate the success of the previous implants. The implant database 622 can be used by the planning module 626 or optimization module 628 to determine a customized implant design, placement, or tool paths for inserting the implant 616 and further customizing the implant components 618b or enabling the creation of a customized kit assembly of implant components 618b. The assembly module 624 designs the implant 616 for a particular patient and the implant components 618b are assembled into a kit which can be used by a surgeon to insert the implant 616 in the patient for whom it was designed. The design process additionally includes the placement of the implant components 618 and the tool paths to be used to insert the implant 616 as well as implantation parameters used during the implantation process. The assembly module 624 triggers the planning module 626 to generate an implantation plan, triggers the optimization module to further customize each implant component 618b for the patient, and further selects an appropriate part from available generic parts or determines that a custom implant component 618 is needed.

In some embodiments, one or more processors generate an implantation plan comprising implantation parameters for controlling insertion of the customized version of the surgical implant 616 into a particular patient's body by the surgical robot 602 of the surgical system of FIG. 6. For example, the planning module 626 images the patient using at least one imaging device 614 and generates the implantation plan. The implantation plan includes a design of the implant 616 and implant placement within a virtual model of a portion of a patient's anatomy or body generated from the images acquired of the patient. The planning module 626 further generates tool paths and implantation parameters to be used during insertion of the implant 616. The optimization module 628 receives information describing an initial implant component 618a from the assembly module 624. The information can be generated by the planning module 622.

In some embodiments, one or more processors of the surgical system of FIG. 6 design a customized version of the surgical implant 616 using patient data describing a particular patient's anatomy or body, a treatment or particular medical application, and the implant database 622. The customized version of the surgical implant 616 comprises at least the generic surgical implant component 618a and the customized surgical implant component 618b. The customized surgical implant component 618b is for the particular patient and the treatment or particular medical application. For example, the optimization module 628 uses data from the implant database 622 to customize the implant component 618b to the patient. An inventory database 630 stores data describing a stock of generic implant components 618a. The implant components 618a can include any of screws, rods, plates, or commercially available implant components. In some embodiments, one or more processors of the system of FIG. 6 determine absence of the customized surgical implant component 618b in an inventory. The one or more processors cause manufacture of the customized surgical implant component 618b in response to determining the absence in the inventory. For example, the inventory database 630 can additionally include manufacturing capabilities to determine whether an implant component 618 can be manufactured. The inventory database 630 can additionally include data on third party vendors including manufacturing capabilities and information necessary to order a custom implant component 618b. The inventory database 630 can include information about tools, instruments, and other equipment associated with surgical procedures.

In some embodiments, a path is generated for a surgical tool 154 in a virtual model of the patient's anatomy or body to virtually insert the customized version of the surgical implant 616 in the virtual model. A virtual robotic surgical procedure is performed according to the implantation plan to virtually insert a model of the customized version of the surgical implant 616 at an implantation site. One or more surgical steps of the implantation plan are simulated using a three-dimensional (3D) model generated using real-time patient data. The 3D model is analyzed in the virtual simulation to determine the implantation parameters. It is determined whether a surgical step of the implantation plan should be performed robotically or by a physician. A virtual simulation is generated using prior patient data for similar surgical procedures. A surgical step is repeatedly simulated using different tool paths and implantation parameters until a simulated surgical step meets approval criteria. Patient data is received upon completion of a surgical step. The patient data is captured by an imaging device 614 in real-time.

FIG. 7 is a table illustrating an example surgical implant database 622, in accordance with one or more embodiments. The implant database 622 is sometimes referred to as a historical treatment database. The implant database 622 (see FIG. 6) stores data from previously inserted implants. In some embodiments, the implant database 622 comprises information describing previously inserted surgical implants. The information comprises at least one of designs of the previously inserted surgical implants, components of the previously inserted surgical implants, surgical tool paths for the previously inserted surgical implants, or operational parameters of surgical tools for the previously inserted surgical implants. The data includes the designs and placement of previous implants, previous tool paths used during implantation procedures, and previous patient information such as gender, age, height, weight, medical conditions, patient medical history, patient family medical history, allergies, or vital information such as baseline measurements of heart rage, blood pressure, blood oxygen saturation, or respiration rate.

The implant database 622 is populated with data from the assembly module 624, medical professionals such as surgeons, physicians, nurses, or physical therapists, or from surveys of previous patient outcomes to evaluate the success of the previous implants. The implant database 622 is used by the planning module 626 or the optimization module 628 to determine an improved implant design, placement, and tool paths for inserting the implant 616. In some embodiments, the surgical robot 602 assembles the generic surgical implant component 618*a* and the customized surgical implant component 618*b* into a kit for inserting the customized version of the surgical implant 616 into a particular patient's body. For example, the implant database 622 is used by the planning module 626 or the optimization module 628 to further customize the implant components 618*b* and generate a kit of implant components 618 to be used during implantation of the implant 616.

Figure 8:
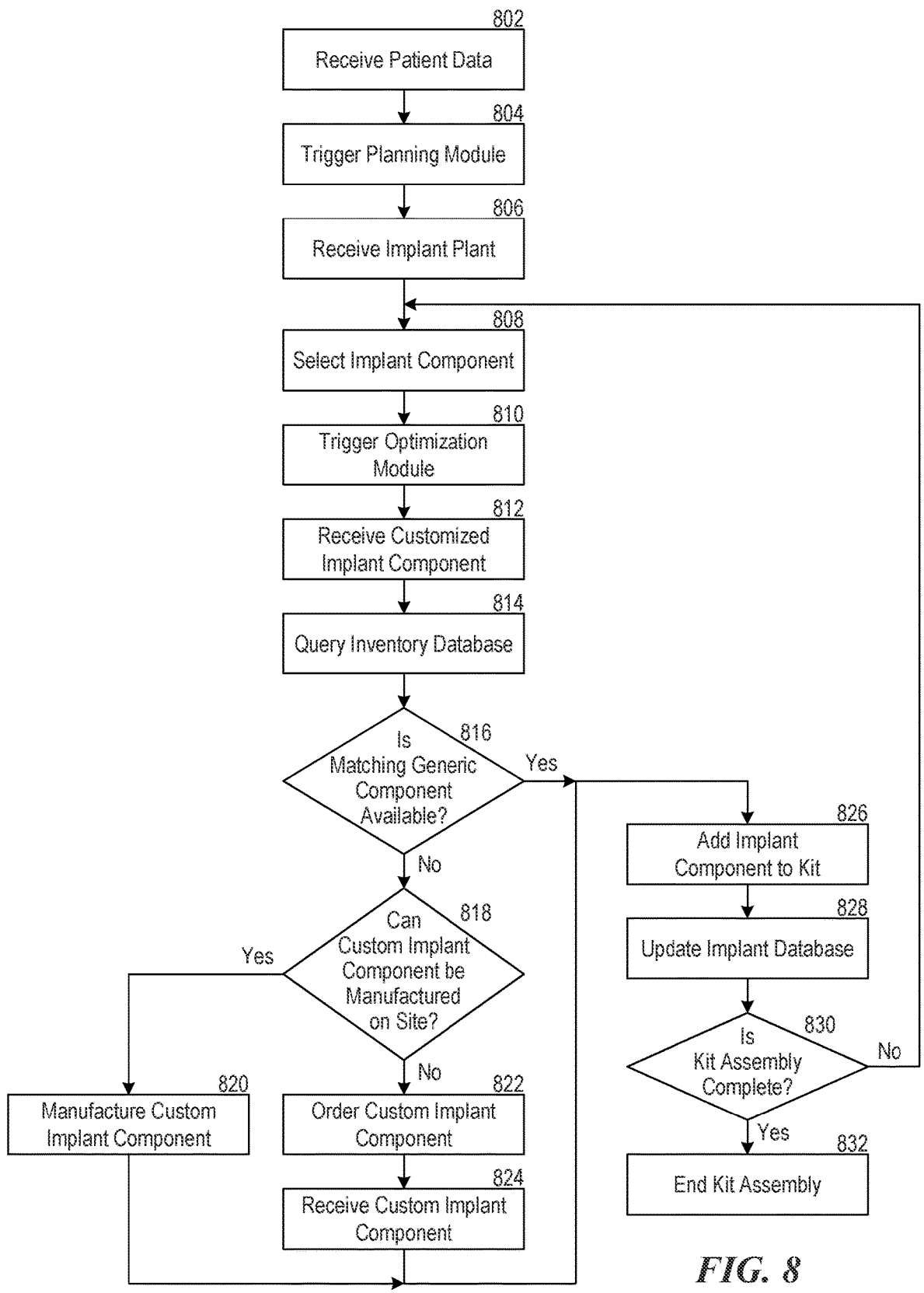
FIG. 8 is a flow diagram illustrating an example process for customized kit assembly for surgical implants, in accordance with one or more embodiments.

FIG. 8 is a flow diagram illustrating an example process for customized kit assembly for surgical implants, in accordance with one or more embodiments. In some embodiments, the process of FIG. 8 is performed by the assembly module 624. The assembly module 624 is illustrated and described in more detail with reference to FIG. 6. In other embodiments, the process of FIG. 8 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 802, the assembly module 624 receives patient data such as gender, age, height, weight, allergies, current or prior medical conditions, or any additional clinical information that can impact the outcome of the surgical procedure. The assembly module 624 further acquires vital information such as the patient's blood pressure, heart rate, blood oxygen saturation, respiration rate, etc. Baseline vital information can be accessed from the clinical information or measured directly. For example, the patient data indicates that the patient is a 57-year-old female who is 66 inches tall and weighs 160 pounds, is allergic to latex and has an osteoporosis diagnosis. The patient data further includes baseline vitals such as a heart rate of 65 beats per minute, blood pressure of 145/105, blood oxygen saturation of 99, and respirations of 6 breaths per minute.

In step 804, the assembly module 624 triggers the planning module 626 (see FIG. 6) to generate an implantation plan for the design, placement, and insertion of the implant 616. The insertion of the implant 616 can be performed manually by a surgeon, with the assistance of the surgical robot 602, or autonomously by one or more surgical robots. Alternatively, the implant 616 can be installed in part by a surgeon, and in part by the surgical robot 602 working autonomously. A surgeon and the surgical robot 602 can further perform actions in a synchronized manner. The planning module 626 generates a virtual model of a portion of the patient's anatomy or body, selects the implant components 618, places models of the implant components 618 in the virtual model, and selects tool paths and implantation parameters to facilitate insertion of the implant 616.

In step 806, the assembly module 624 receives the implantation plan from the planning module 626. The implantation plan specifies at least one implant 616 that includes at least one implant component 618*a*, the placement of models of the implant components 618 in a virtual model of the patient, and the paths that surgical tools 154 (see FIG. 1) and the implant components 618 will take within the body of the patient during a surgical procedure to insert the implant 616. For example, the implant components 618 include 6 screws, each having a tulip head, two rods, and two plates, each made of titanium. The 6 screws are to be inserted 1 inch each into three vertebrae, one screw on either side of the spinous process on each vertebra.

In step 808, the assembly module 624 selects an implant component 618*a* or 618*b* from the implant components 618 specified in the implantation plan. For example, the implant component 618*a* is a screw with a tulip head. In another example, the implant component 618*a* is a rod. In another example, the implant component 618*a* is a plate. In a further example, the implant component 618*b* is a customized volume or bracket.

In step 810, the assembly module 624 triggers the optimization module 628, which receives information describing the implant component 618*a* and placement data. The optimization module 628 further receives tool paths and implantation parameters to be used when inserting the implant component 618*a*. The optimization module 628 retrieves patient data and utilizes data from the implant database 622 to determine the best materials and physical features for the implant component 618a for the patient. For example, the optimization module 628 receives information specifying a screw having a tulip head intended to be installed 1 inch left of the spinous process of the T6 vertebra as part of the implant 616 to complete a fusion 360 procedure.

In step 812, the assembly module 624 receives information describing a customized implant component 618b from the optimization module 628. The implant component 618b can be modified by the optimization module 628 using patient data and data from previously inserted implants 616 from the implant database 622 to better accommodate the patient's physiology including allergies and medical conditions. For example, a patient has osteoporosis and therefore a screw meant to be used in the implant 616 is elongated from 1 inch to 1.5 inches and the threads per inch are reduced from 24 to 18. The screw can further be modified by adjusting a gage, length, size or shape of the head, type of head, or the pitch, thread angle, minor diameter, or major diameter of the threads. Similarly, the material can be changed from surgical stainless steel to titanium or a titanium alloy. Similarly, a rod or plate can be altered by adding or changing a bend in the rod or plate. The rod can further be modified with a complex curve or a plate can be modified with a more complex geometry or replaced by a volume.

In step 814, the assembly module 624 queries the inventory database 630 for a stock of generic or otherwise in-stock implant components 618a. In an embodiment, the in-stock generic implant components 618a include screws of various sizes ranging from 0.5 inches to 3 inches having a range of standard and metric threads with tulip heads and traditional rounded star heads. The screws can alternatively be comprised of proprietary designs. The inventory database 630 can additionally include an inventory of rods and plates. The rods can be available in a range of diameters and lengths and the plates can similarly be available in a range of dimensions and can have holes and other features to accept screws and other hardware. The implant components 618a can additionally be available in a range of materials such as surgical stainless steel and titanium or alloys. The inventory database 630 can also contain the manufacturing capabilities and order information for third party vendors in order to enable ordering of custom implant components 618b from third party sources.

In step 816, the assembly module 624 determines whether the customized implant component 618b matches an implant component 618a in stock according to the inventory database 630. A matching implant component 618a can be an exact match or can match required design parameters while not necessarily matching optional design parameters. For example, the customized implant component 618b is a 1.5-inch titanium screw having 18 threads per inch and a tulip head. The assembly module 624 determines that the screw is immediately available as indicated by a Quantity of 5 returned by the inventory database 630. Alternatively, the material is optional and the screw is available in stainless steel; therefore, the assembly module 624 selects the stainless steel alternative as a matching generic component. In another example, the titanium material is not optional, and therefore a generic component is not available.

In step 818, the assembly module 624 determines whether a custom implant can be manufactured on-site by retrieving the manufacturing capabilities for the present site from the inventory database 630 and comparing the manufacturing capabilities to the process required to manufacture the implant component 618b. For example, the implant component 618b is a screw and requires casting. In step 818, the assembly module 624 determines that casting is not available on site and therefore the custom implant component 618b cannot be manufactured on site. Alternatively, the assembly module 624 determines that the screw can be machined and that a 5-axis CNC mill is available on site and therefore the implant component 618b can be manufactured on site.

In step 820, the assembly module 624 enables manufacturing of the custom implant component 618b as designed by the optimization module 628, e.g., by the surgical robot 602 or other machinery. The manufacturing can be performed in the operating room 102 (see FIG. 1), in a staging or preparation area adjacent to the operating room 102, or in a facility on the same premises as the operating room 102. Alternatively, the custom implant component 618b can be manufactured in a nearby facility or remote location. The custom implant component 618b can be immediately available for installation upon completion or can alternatively be tested prior to installation. In some embodiments, causing the manufacture of the customized surgical implant component 618b comprises enabling additive manufacturing of the customized surgical implant component using a laser sintering three-dimensional (3D) printer or machining the customized surgical implant component using a computer numerical control (CNC) machine. For example, the custom implant component 618b is a screw manufactured via additive manufacturing via a laser sintering 3D printer in a preparation area adjacent the operating room 102. The manufacturing additionally uses a 5-axis CNC mill to remove burrs and uneven surfaces and adds features such as a tulip head by removing material from the 3D printed screw. Further examples include the modification of a generic implant component 618a such as adding threads to a generic rod, or bending a rod or plate.

The optimization module 628 can generate parameters, dimensions, and/or instructions or files for manufacturing items, such as customized implant components 618b. In some embodiments, the optimization module 628 generates a three-dimensional model of the customized implant component 618b that is transmitted to an onsite or offsite manufacturing system. Example manufacturing system can include, without limitation, one or more printers (e.g., additive manufacturing printers), milling machines, molding machines, lathes, extruders, and/or other manufacturing equipment disclosed herein. In some embodiments, the optimization module 628 generates three-dimensional CAD or CAM models that are transmitted to the manufacturing system. The manufacturing system can determine manufacturing instructions executable to manufacture the customized implant component 618b. In some embodiments, the optimization module 628 generates and send machine executable instructions to instruct the manufacturing equipment to produce the customized implant component 618b.

In some embodiments, one or more processors of the system of FIG. 6 determine the absence of the customized surgical implant component 618b in an inventory. For example, in step 822, the assembly module 624 can order a custom implant component 618b if the manufacturing capabilities required to manufacture the implant component 618b do not exist on site. Similarly, the assembly module 624 orders the custom implant component 618b if there is insufficient stock of raw materials on site. The assembly module 624 orders a compatible generic component 618a that is not immediately available according to the inventory database 630. For example, the implant component 618b is a screw requiring a casting of titanium and such capabilities are unavailable on site. Thus, the assembly module 624 orders the screw from a third-party vendor.

In step 824, the assembly module 624 receives information indicating that the custom implant component 618*b* has been delivered from a third-party vendor. The implant component 618*b* can be delivered via a commercial delivery service or courier. The assembly module 624 enables inspecting and testing the implant component 618*b* to ensure that the implant component 618*b* matches the design specification identified by the optimization module 628. For example, the implant component 618*b* is a 1.5-inch titanium screw with 18 threads per inch and a tulip head and the inspection process includes visual inspection and testing that the thread is compatible with the receiving hardware such as a rod intended to be mated to the tulip head of the screw.

In step 826, the assembly module 624 adds the implant component 618*b* to the kit. For example, the implant component 618*b* can be a screw, rod, plate, or volume. In another example, the implant component 618*b* can be a tool or accessory for use during an implantation procedure to enable the insertion of the implant component 618*b*.

In step 828, the assembly module 624 updates the implant database 622 with the implant component 618*b*, its design specifications, and whether the part was sourced from available generic components 618*a* or alternatively was custom manufactured. In step 824, the assembly module 624 further indicates the implant 616 of which the implant component 618*b* is a part and the patient in whom it is to be installed. Additionally, the assembly module 624 updates the implant database 622 with any tool paths and implantation parameters which can be used to install the implant component 618*b*. For example, the database 622 is updated with a 1.5-inch titanium screw with 18 threads per inch and a tulip head to be implanted in a 66-inch tall, 57-year-old female with osteoporosis.

In step 830, the assembly module 624 determines whether the kit assembly is complete. The kit assembly is complete if there are no remaining implant components 618 or tools in the implantation plan that need to be selected and added to the kit. If more implant components 618 remain, the assembly module 624 returns to step 808 and selects another implant component from the implantation plan. For example, additional implant components 618 remain, therefore the kit assembly is not complete.

In step 832, the assembly module 624 terminates the kit assembly when all implant components 618 and tools in the implantation plan have been selected, customized, and added to the kit.

The method of FIG. 8 can be used to assemble implant kits, instrument kits, and other surgical kits. Example implant kits can include, without limitation, an instrument tray or case containing one or more assembled or unassembled implants. Example instrument kits can include, without limitation, an instrument tray or case containing one or more cannulas, obturators, hooks, scissors, clips, spreaders, scalpels, alignment guides (e.g., scope guides, endoscope guides, bronchoscope guides), drivers, irrigators, cautery hooks, dissectors, etc. Example surgical kits can contain, without limitation, one or more implants, instruments, and other items and components disclosed herein. Examples of surgical implants include, but are not limited to, screws (e.g., locking screws, spinal screws, pedicle screws, bone screws, facet screws), interbody implant devices (e.g., intervertebral implants, cages), fusion devices, plates, rods, disks (e.g., an artificial articulating disk), spacers (e.g., interspinous spacers, fixed body spacers), rods, expandable devices, stents, brackets, ties, scaffolds, fixation devices (e.g., plates/rod/screw assemblies, anchor plates, etc.), bolts, fasteners, joint replacements, knee joints, hip implants, or the like. Examples of instruments include, but are not limited to, cannulas, ports, imaging devices, screw guides, spreaders, insertion tools, or the like. Kits can be assembled locally (e.g., onsite at a healthcare facility, a surgical room, or another suitable location) using local inventory, locally manufactured items, off-site manufactured items, etc. The kits can be sterilized and then provided to the surgical team. FIG. 4A shows two surgical kits 453*a*, 453*b* in the surgical room for performing surgical procedures and can include components discussed herein.

The methods disclosed herein can include receiving, via a computer system, patient data of the patient, monitoring data, and other data disclosed herein. The computing system can determine a patient-sized component based on the received patient data. The received patient data can include, without limitation, images, physician notes, or other patient data disclosed herein. The computing system can determine whether the patient-sized component is in inventory based on an inventory database 630. The inventory database 630 can include a number of implants, manufacturer information, sizes of implants, implant components, and other inventory information. For example, the inventory database 630 includes a list of available implants of different sizes for a particular procedure. The computing system can determine whether the patient-sized components in inventory are suitable for a planned procedure.

In response to determining that a suitable patient-sized component is not in inventory, the computing system can cause a suitable patient-sized component to be acquired. In some embodiments, in response to determining that the patient-sized component is absent from the inventory, the computing system causes the patient-sized component to be manufactured. Advantageously, the patient-sized component can be customized to the patient's dimensions to provide a patient-specific component, implant, instrument, etc.

In response to the patient-sized component being in inventory, the computing system can analyze scheduled procedures for other patients to identify one or more of the scheduled procedures in which the patient-sized components are suitable. The computing system can prioritize and assign the available patient-sized components to the appropriate patients. The computing system can then cause additional patient-sized components (e.g., standard or patient-specific components) to be ordered or manufactured for other patients. This allows for flexibility when scheduling procedures and selecting suitable components of kits.

In some embodiments, the computing system determines whether to reserve a patient-sized component for the identified one or more patients based on the number of patient-sized components being in inventory and predicted outcomes for each of the one or more patients. The outcomes can be used to assign patient components to patients. For example, if the predicted outcome for a patient is below a threshold score, the computing system can develop an implantation plan and design one or more patient-specific components to increase the outcome score for the procedure. This allows the computing system to ensure that predicted outcomes for scheduled procedures are predicted to be at or above a threshold outcome score.

The computing system can also analyze surgical plans to determine one or more steps of the surgical plan based on an identified surgical robot scheduled for surgery. The components can be assembled into a surgical kit used by the surgical team to prepare the surgical robot for surgery. In some embodiments, the computing system can determine potential adverse events, alternative surgical steps, component malfunction, etc. and recommend auxiliary or stand-by kits. The auxiliary or stand-by kits can include, without limitation, one or more instruments, implants, components of implants (e.g., unassembled implants, partially assembled implants, etc.), robotic tools, surgical equipment, or combinations thereof.

In some embodiments, the system identifies one or more components in inventory suitable for a surgical plan based on virtual modeling or simulations. The system can select the components (e.g., patient-sized components, patient-specific components, etc.) based on compatibility of the patient-sized component with other available components for a surgical kit. For example, the system can perform simulations using available equipment (e.g., surgical instruments in inventory). Based on the simulations, the system can determine additional instruments, implants, or other equipment suitable for the procedure. This enables the system to provide surgical kits based on available components according to the surgical plan. The system can base the analysis on historical treatment information retrieved from a historical treatment database.

For pre-operative kit assemblies, the system can schedule manufacturing of components of kits such that the kits can be assembled and sterilized before scheduled start times for surgical procedures. If the system receives notification of manufacturing delays, the surgical system can automatically notify the healthcare provider, patient, and other individuals to reschedule the surgery. In some embodiments, the healthcare provider schedules surgical procedures based on a manufacturing schedule for patient-sized components, the patient conditions, or other input parameters. Manufacturing schedules can be modified based on the priority of the conditions of the scheduled patients. This allows flexibility to prioritize patients based on the condition of the patients. For intra-operative kit assemblies, the system can determine the number and configuration of kits to be provided based on, for example, real-time monitoring data, identified events, and/or physician input (e.g., input for new surgical steps, alternative techniques, etc.). For example, unplanned adverse event(s) may require additional surgical steps to be performed. The system can design in real-time kits for those surgical steps using on-site manufacturing equipment. The system can intra-operatively design components of the kit based on the on-site manufacturing capabilities. In some embodiments, the system can determine risk scores for adverse event(s), or other events, during the surgical procedure and can provide surgical kits (or components of kits) when the risk score(s) reach threshold score(s). The surgical kits are then available if needed by the surgical team. In such procedures, the system may include manufacturing equipment near to or at the surgical room. The system can receive data before and/or during the surgical procedure and can use received data to, for example, recommend, design (pre-operatively and/or intra-operatively design), and/or provide components, implants, instructions, and/or kit assemblies.

Figure 9:
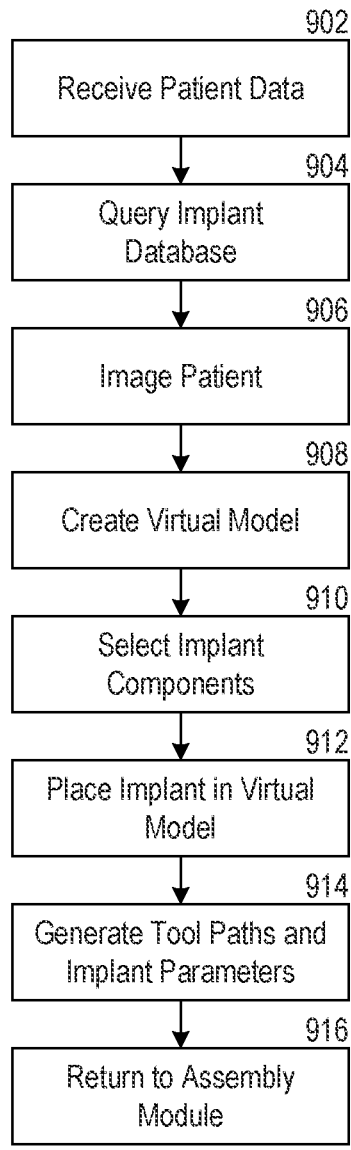
FIG. 9 is a flow diagram illustrating an example process for customized kit assembly for surgical implants, in accordance with one or more embodiments.

FIG. 9 is a flow diagram illustrating an example process for customized kit assembly for surgical implants, in accordance with one or more embodiments. In some embodiments, the process of FIG. 9 is performed by the planning module 626. The planning module 626 is illustrated and described in more detail with reference to FIG. 6. In other embodiments, the process of FIG. 9 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 902, the planning module 626 receives patient data from the assembly module 624. The patient data includes any of gender, age, height, weight, allergies, current or prior medical conditions, or any additional clinical information which may impact the outcome of the implantation procedure. Patient data can additionally include vital information such as the patient's blood pressure, heart rate, blood oxygen saturation, respiration rate, etc. For example, the patient data indicate that the patient is female, 66 inches tall, and has osteoporosis.

In step 904, the planning module 626 queries the implant database 622 for data from previously installed implants 616. The data includes previous designs for implants, previous implant components, previous implantation parameters, and previous tool paths. The implantation parameters retrieved can include direction and speed of movement of a previous surgical tool or implant component as well as operational parameters such as rotational speed or axial force exerted by the tool or implant component, and tool alignment. For example, an example of data stored in the implant database 622 describes a screw that is 2 inches long with a diameter of 0.25 inches and is made of stainless steel. The data can further describe that the screw has 24 threads per inch and is installed one inch to the left of the spinous process in the T-6 vertebra of a 75-inch tall, 64-year-old male. Further, the screw was inserted with a rotational speed of 25 rotations per minute, an axial force of 3 pounds per square inch, and an alignment angle of 15 degrees off center.

In step 906, the planning module 626 enables imaging the patient using at least one imaging device 614 such as magnetic resonance imaging, computer aided tomography, or ultrasound. The imaging includes at least the site on the patient's body receiving the implant 616 and a surrounding area. Alternatively, the imaging includes the entirety of the patient's body. In some embodiments, generating the images of a portion of the particular patient's body comprises capturing image slices of the portion of the particular patient's body at different depths using magnetic resonance imaging (MRI) and layering the image slices to provide a 3D virtual model. For example, the patient is imaged using magnetic resonance imaging such that multiple images are taken representing slices at varying depths.

In some embodiments, generating an implantation plan comprises generating, by one or more processors of the system of FIG. 6, a virtual model of a portion of a particular patient's body based on the images. The one or more processors place a model of the customized version of the surgical implant 616 in the virtual model to determine the implantation parameters. The implantation parameters comprise a speed of inserting the customized surgical implant component 618b into the portion of the particular patient's body and a force applied to the customized surgical implant component 618b. For example, in step 908, the planning module 626 generates a virtual model of a portion of the patient's body using the images captured of the patient using the at least one imaging device 614. The virtual model can be two dimensional or three dimensional. In some embodiments, one or more processors of the system of FIG. 6 animate the 3D virtual model using movement of the particular patient's body over time to provide a four-dimensional (4D) virtual model. The virtual model can include a fourth dimension of time such that the model can be animated to represent movement of the patient's body over a period of time. For example, multiple magnetic resonance imaging slices are layered to create a three-dimensional virtual model of the patient's spine and surrounding tissues in preparation of performing a spinal 360 fusion procedure via the insertion of an implant 616 fusing three vertebrae together.

In step 910, the planning module 626 selects the implant components 618 which will make up the implant 616. The implant 616 can include a single implant component 618*a* or an assembly of multiple implant components 618. An assembly can be implanted as a single unit or can require implantation in multiple discrete pieces to form the final implant 616. Use of an assembly can improve functionality of the implant 616, such as articulation or flexibility, or can facilitate the insertion of the implant 616 such that the assembled implant 616 is more rigid with little or no flexibility. Selection of the implant components 618 further includes selecting the material which each implant component 618*a* is to be made of. For example, the implant components 618 make up a spinal implant 616 and include six screws, each with a head known as a "tulip" to receive one of two rods and two plates to join the two rods together to prevent movement relative to one another. All of the implant components 618 are made of titanium.

In step 912, the planning module 626 places a model of the at least one implant 616 in or on the virtual model of the patient's body. The model of the implants 616 are placed in the virtual model as they would be by a surgeon or the surgical robot 602 in or on the patient's body. For example, a spinal implant is inserted into a three-dimensional model of a patient's thoracic spine to fuse three vertebrae to one another. The spinal implant includes at least two screws inserted 1 inch into each vertebra, one on either side of the spinous process and perpendicular to the surface of the vertebrae. Additionally, two rods located on either side of the spinous process are each secured to the screws on its respective side of the spinous process via a tulip. Two plates connect the two rods to one another to prevent the rods from moving relative to one another.

In step 914, the planning module 626 generates tool paths and implantation parameters for each implant component 618. The implantation parameters action as instructions for a surgeon or the surgical robot 602 to aid the insertion of the implant components 618 and can additionally include design parameters to be used in the selection of an implant component 618*a* or the manufacture of custom implant components 116*b*. In some embodiments, the end effector 606 of the surgical robot 602 inserts the customized version of the surgical implant 616 from the kit into a portion of a particular patient's body for a particular treatment or medical application or procedure according to the implantation parameters. For example, a tool path includes moving a rod, for implantation along the spine of the patient, into the incision site and parallel to the spine until it is in position alongside the spinous process and above the screws. The rod is further engaged with the tulip on the head of each screw. In step 914, the planning module 626 further generates implantation parameters, such as the rate of movement of an implant component 618*a* through the patient's body, the orientation of the implant component 618*a*, and the force which should be applied to engage the rod with the screws. For example, the planning module 626 specifies that the implant component 618*a* should be moved within the patient's body by pushing the rod lengthwise into the incision to the surgical site until it is in position at a rate not to exceed 2 inches per minute. Continuing the example, when the rod is positioned above the screws it is intended to engage, the planning module 626 specifies that a force should be applied perpendicular to the rod not to exceed 5 pounds per square inch until the rod engages the screw heads. Further, the rod should be 3.5 inches long and 0.375 inches in diameter.

In step 916, the planning module 626 returns control to the assembly module 624 when the implant components 618 have been selected and placed in a virtual model of the patient, and the tool path, implantation parameters, design of the implant components 618, and manufacturing parameters have been generated. The implant components 618, their placement, the tool paths, implantation parameters, and the design and manufacturing parameters for the implant components 618 are included in an implantation plan.

Figure 10:
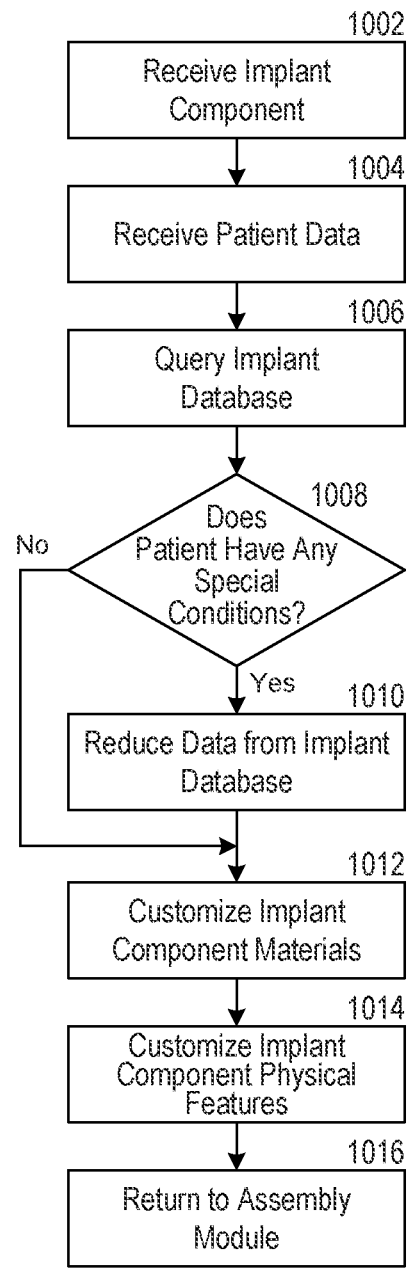
FIG. 10 is a flow diagram illustrating an example process for customized kit assembly for surgical implants, in accordance with one or more embodiments.

FIG. 10 is a flow diagram illustrating an example process for customized kit assembly for surgical implants, in accordance with one or more embodiments. In some embodiments, the process of FIG. 10 is performed by the optimization module 628. The optimization module 628 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the optimization module 628 receives information describing an implant component 618 from the assembly module 624. The implant component 618 is specified by an implantation plan generated by the planning module 626. The information describing the implant component 618 includes parameters such as the type of component and physical dimensions, and can further specify the material and manufacturing process. The information describing the implant component 618 can additionally include tool paths and implantation parameters to be used by a surgeon or the surgical robot 602 to insert the implant component 618. For example, the implant component 618 is a screw with a tulip head intended to be installed 1 inch to the left of the spinous process of the T6 vertebra as part of an implant 616 to perform a fusion 360 procedure. The screw is 1 inch long with 24 threads per inch.

In step 1004, the optimization module 628 receives patient data indicating any of gender, age, height, weight, allergies, current or prior medical conditions, or any additional clinical information that can impact the outcome of the implantation procedure. Patient data can additionally include vital information such as the patient's blood pressure, heart rate, blood oxygen saturation, respiration rate, etc. The patient data can additionally describe the virtual model created by the planning module 626. For example, the patient data indicates that the patient is female, 66 inches tall, and has osteoporosis.

In step 1006, the optimization module 628 queries the implant database 622 for data from previously installed implants. The data retrieved can include designs for previously inserted implants, the previous implant components, previous implantation parameters, and tool paths. The implantation parameters can include the direction and speed of movement of a previously used surgical tool 154 or implant component as well as operational parameters such as rotational speed, axial force exerted by the tool 154, or tool alignment. For example, an example of data stored in the implant database 622 describes a screw that is 2 inches long with a diameter of 0.25 inches and is made of stainless steel. The data can further specify that the screw has 24 threads per inch and is installed one inch to the left of the spinous process in the T6 vertebra of a 75-inch tall, 64-year-old male. Further, the screw was inserted with a rotational speed of 25 rotations per minute, an axial force of 3 pounds per square inch, and an alignment angle of 15 degrees off center.

In step 1008, the optimization module 628 determines whether the patient data indicates that the patient has any special medical conditions such as osteoporosis, hypertension, hypotension, anemia, etc., that can impact the type of implant 616 used, how the implant 616 is to be secured within the patient's body, or adjustments which can need to be made to tool pathing to accommodate the patient's conditions. For example, the patient is confirmed to have osteoporosis.

In step 1010, the optimization module 628 reduces the data set retrieved from the implant database 622 by applying a filter for patients receiving implants who have been diagnosed with the same special conditions afflicting the current patient. For example, the optimization module 628 filters the data from the implant database 622 for previous implants installed in patients who were also diagnosed with osteoporosis. In further embodiments, the data set can be expanded if insufficient data remains after applying a filter such as age, gender, weight, height, etc.

In step 1012, the optimization module 628 customizes the implant component 618's materials. The materials can include any of metal, metal alloy, plastic, ceramic, etc., that have been deemed safe for implantation into a patient's body. The implant component 618 can include a single material, or alternatively, an assembly of multiple materials, such as a screw made of surgical steel with a movable tulip head which can be made of a titanium alloy. The material being customized is based on factors including patient allergies, a need to maximize strength of the implant component 618, a feature of the implant component 618, or a need to minimize the size of the implant component 618. For example, a screw is customized by selecting titanium instead of stainless steel to increase strength while reducing size. Customizing the implant component 618's materials can further provide for a method of manufacture, such as whether the implant component 618 should be formed via casting, extrusion, milling, etc. For example, the optimization module 628 indicates that a screw should be formed via laser sintering additive manufacturing, or alternatively, via milling.

In some embodiments, designing the customized version of the surgical implant 616 comprises determining a length, width, and height of the customized surgical implant component 618*b*. In some embodiments, designing the customized version of the surgical implant 616 comprises determining threads or a head of a screw of the customized surgical implant component 618*b*. In some embodiments, designing the customized version of the surgical implant 616 comprises determining a cut or a bend of the customized surgical implant component 618*b*. For example, in step 1014, the optimization module 628 customizes the implant component 118's physical features. The physical features can include physical dimensions such as length, width, height or depth, diameter, etc. The physical features can additionally refer to elements of the implant component 618, such as the threads or head of a screw. The physical features can additionally include cuts, bends, or other physical modifications to the implant component 618. The implant component 618 can be customized based on factors including patient conditions such as osteoporosis, strength of the implant component 618, a feature of the implant component 618, or the size of the implant component 618.

For example, a patient has osteoporosis and therefore a screw is elongated from 1 inch to 1.5 inches and the threads per inch are reduced from 24 to 18. A screw can further be altered by adjusting the gage, length, size or shape of the head, or type of head. A screw can further be altered by adjusting the pitch, thread angle, minor diameter, or major diameter of the threads. Similarly, a rod or plate can be altered by adding or changing a bend in the rod or plate. A rod can further be modified with a complex curve, or a plate be given a more complex geometry or be replaced by a volume. Customization of an implant component 618's physical features can further provide for a method of manufacture, such as whether the implant component 618 should be formed via casting, extrusion, milling, etc. For example, in step 1014, the optimization module 628 further indicates that a screw should be formed via milling.

In step 1016, the optimization module 628 returns information describing the customized implant component 618 to the assembly module 624. The information describing the customized implant component 618 specifies materials, physical features, or methods of manufacture of the customized implant component 618. For example, the customized implant component 618 is a 1.5-inch-long titanium screw with 18 threads per inch.

Figure 11:
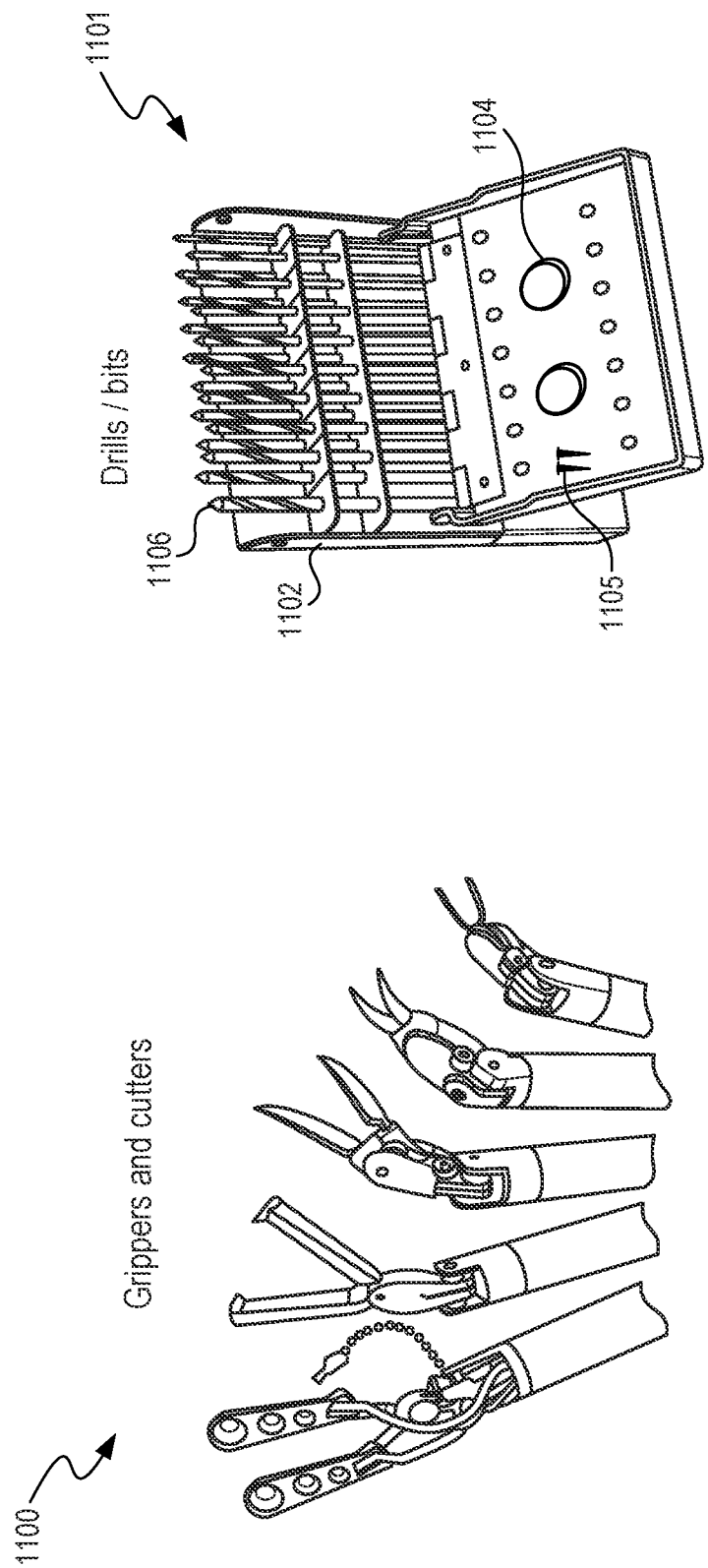
FIG. 11 illustrates kit components, in accordance with one or more embodiments.

FIG. 11 illustrates end effectors for kits, according to an embodiment. The end effectors 1100 can be installed in the robotic systems disclosed herein. The end effectors can include, without limitation, robotic grippers (illustrated), cutting instruments (e.g., cutters, scalpels, or the like), drills, cannulas, reamers, rongeurs, scissors, clamps, drills, bits, or the like. The number and configuration of end effectors can be selected based on the configuration of the robotic system and the procedure to be performed. The systems disclosed herein select end effectors to perform one or more the steps in a surgical procedure and can provide kits. Surgical kit 1101 includes a tray/case 1102 holding implants 1104 (e.g., customized implants), screws 1105, drills 1106 (one identified), bits, etc. The configuration, components, and features of the surgical kit 1101 can be selected based on the surgery and procedures to be performed.

The functions performed in the processes and methods can be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A method comprising:
   receiving, by one or more processors, images of a portion of a patient's body for implanting a surgical implant in the patient's body for a treatment;
   selecting, by the one or more processors, at least one generic surgical implant component and at least one customized surgical implant component for the surgical implant based on the received images and a historical treatment database, wherein the at least one customized surgical implant component is configured for the patient and the treatment;
   determining, by the one or more processors, absence of the at least one customized surgical implant component in an inventory;
   in response to determining the absence of the at least one customized surgical implant component, causing, by the one or more processors, manufacture of the at least one customized surgical implant component; and
   assembling a surgical kit including the at least one generic surgical implant component from the inventory and the manufactured at least one customized surgical implant component, wherein the surgical kit is configured to implant the surgical implant using a surgical robot.

2. The method of claim 1, wherein the historical treatment database comprises information describing previously inserted surgical implants, the information comprising at least one of designs of the previously inserted surgical implants, components of the previously inserted surgical implants, surgical tool paths for the previously inserted surgical implants, or operational parameters of surgical tools for the previously inserted surgical implants.

3. The method of claim 1, wherein the at least one customized surgical implant component is configured for the patient's anatomy based on at least one of:
   a length, width, and height of the at least one customized surgical implant component;
   thread size or a head of a screw of the at least one customized surgical implant component; or
   a cut or a bend of the at least one customized surgical implant component.

4. The method of claim 1, further comprising:
   generating, by the one or more processors, a virtual model of the portion of the patient's body based on the images;
   placing, by the one or more processors, a model of the surgical implant in the virtual model to determine one or more implantation parameters, wherein the one or more implantation parameters comprise a speed of inserting the at least one customized surgical implant component into the portion of the patient's body and a force applied to the at least one customized surgical implant component during the insertion;
   generating, by the one or more processors, an implantation plan comprising the determined one or more implantation parameters for implanting the surgical implant into the patient's body using the surgical robot; and
   inserting, by an end effector of the surgical robot, the at least one generic surgical implant component and the at least one customized surgical implant component into the portion of the patient's body according to the one or more implantation parameters.

5. The method of claim 4, wherein the images of the portion of the patient's body comprise image slices of the portion of the patient's body at different depths generated using magnetic resonance imaging (MRI) and the virtual model comprises a three-dimensional (3D) layering of the image slices.

6. The method of claim 4, further comprising:
   animating, by the one or more processors, the virtual model using movement of the patient's body over time to provide a four-dimensional (4D) virtual model.

7. The method of claim 1, wherein causing the manufacture of the at least one customized surgical implant component comprises enabling at least one of:
   additive manufacturing of the at least one customized surgical implant component using a laser sintering three-dimensional (3D) printer; or
   machining the at least one customized surgical implant component using a computer numerical control (CNC) machine.

8. A system comprising:
   one or more computer processors; and
   a non-transitory computer-readable storage medium storing computer instructions, which when executed by the one or more computer processors, cause the system to:
      receive images of a portion of a patient's body for implanting a surgical implant in the patient's body for a treatment;
      select at least one generic surgical implant component and at least one customized surgical implant component for the surgical implant based on the received images and a historical treatment database, wherein the at least one customized surgical implant component is configured for the patient and the treatment;
      determine absence of the at least one customized surgical implant component in an inventory;
      in response to determining the absence of the at least one customized surgical implant component, cause manufacture of the at least one customized surgical implant component; and assemble a surgical kit including the at least one generic surgical implant component from the inventory and the manufactured at least one customized surgical implant component, wherein the surgical kit is configured to implant the surgical implant using a surgical robot.

9. The system of claim 8, wherein the historical treatment database comprises information describing previously inserted surgical implants, the information comprising at least one of designs of the previously inserted surgical implants, components of the previously inserted surgical implants, surgical tool paths for the previously inserted surgical implants, or operational parameters of surgical tools for the previously inserted surgical implants.

10. The system of claim 8, wherein the at least one customized surgical implant component is configured for the patient's anatomy based on at least one of:
   a length, width, and height of the at least one customized surgical implant component;
   thread size or a head of a screw of the at least one customized surgical implant component; or
   a cut or a bend of the at least one customized surgical implant component.

11. The system of claim 8, wherein the computer instructions further cause the system to:
   generate a virtual model of the portion of the patient's body based on the images;
   place, a model of the surgical implant in the virtual model to determine one or more implantation parameters, wherein the one or more implantation parameters comprise a speed of inserting the at least one customized surgical implant component into the portion of the patient's body and a force applied to the at least one customized surgical implant component during the insertion;
   generate an implantation plan comprising the determined one or more implantation parameters for implanting the surgical implant into the patient's body using the surgical robot; and
   insert, by an end effector of the surgical robot, the at least one generic surgical implant component and the at least one customized surgical implant component into the portion of the patient's body according to the one or more implantation parameters.

12. The system of claim 11, wherein the images of the portion of the patient's body comprise image slices of the portion of the patient's body at different depths generated using magnetic resonance imaging (MRI) and the virtual model comprises a three-dimensional (3D) layering of the image slices.

13. The system of claim 11, wherein the computer instructions further cause the system to:
   animate the virtual model using movement of the patient's body over time to provide a four-dimensional (4D) virtual model.

14. The system of claim 8, wherein the computer instructions to cause the manufacture of the at least one customized surgical implant component cause the system to enable at least one of:
   additive manufacturing of the at least one customized surgical implant component using a laser sintering three-dimensional (3D) printer; or
   machining the at least one customized surgical implant component using a computer numerical control (CNC) machine.

15. A computer-implemented method comprising:
   selecting at least one generic surgical implant component and at least one customized surgical implant component for a surgical implant based on a historical treatment database and images of a portion of a patient's body for implanting the surgical implant in the patient's body for a treatment, wherein the at least one customized surgical implant component is configured for the patient and the treatment;
   in response to determining the absence of the at least one customized surgical implant component in an inventory, causing manufacture of the at least one customized surgical implant component; and
   assembling a surgical kit including the at least one generic surgical implant component from the inventory and the manufactured at least one customized surgical implant component, wherein the surgical kit is configured to implant the surgical implant using a surgical robot.

16. The computer-implemented method of claim 15, further comprising generating, by one or more imaging devices, the images of the portion of the patient's body.

17. The computer-implemented method of claim 15, further comprising generating a path for a surgical tool in a virtual model of the patient's body to virtually insert the surgical implant in the virtual model.

18. The computer-implemented method of claim 15, further comprising performing a virtual robotic surgical procedure according to an implantation plan to virtually insert a model of the surgical implant at an implantation site.

19. The computer-implemented method of claim 18, further comprising:
   virtually simulating one or more surgical steps of the implantation plan using a three-dimensional (3D) model generated using real-time patient data; and
   analyzing the virtual simulation to determine the implantation parameters.

20. The computer-implemented method of claim 18, further comprising determining whether a surgical step of the implantation plan should be performed robotically or by a physician.

* * * * *